United States Patent [19]

Kowalski

[11] 4,413,351
[45] Nov. 1, 1983

[54] COMPUTER TOMOGRAPHY APPARATUS

[75] Inventor: Günter Kowalski, Rellingen, Fed. Rep. of Germany

[73] Assignee: U.S. Philips Corporation, New York, N.Y.

[21] Appl. No.: 248,631

[22] Filed: Mar. 27, 1981

[30] Foreign Application Priority Data

Apr. 1, 1980 [DE] Fed. Rep. of Germany ....... 3012648

[51] Int. Cl.³ .............................................. G03B 41/16
[52] U.S. Cl. ..................................... 378/19; 364/414; 378/901
[58] Field of Search ................... 378/19, 901; 364/414

[56] References Cited

U.S. PATENT DOCUMENTS 4,138,610 2/1979 Weinkauf ............................... 378/19
4,220,860 9/1980 Carlson .................................. 378/19

Primary Examiner—Craig E. Church
Attorney, Agent, or Firm—Jack E. Haken

[57] ABSTRACT

A computer tomography device which comprises means in at least a part of its detector array (5), for forming a difference measurement value between each pair of adjacent detectors which is proportional to the difference of the non-amplified detector output signals. At least one detector of this part is additionally connected to further means (14) which produce an absolute measurement value which is proportional to its detector output signal. Adding means add the difference measurement values to the absolute measurement value.

8 Claims, 6 Drawing Figures

COMPUTER TOMOGRAPHY APPARATUS

FIELD OF THE INVENTION

The invention relates to a device for determining the absorption distribution of radiation in a flat examination zone in a body, comprising a radiation source which is rotatable about the body and which is arranged to emit a fan-shaped radiation beam which extends in the plane and which completely irradiates the examination zone in different directions, and also comprising a detector array which comprises individual detectors for generating detector output signals which are a measure of the absorption of radiation and which are amplified and applied, via analog-to-digital converters, to an electronic unit for generating and displaying the absorption distribution from the detector output signals.

Devices of this kind (computer tomography apparatus) are generally known, from German Offenlegungsschrift No. 26 25 312. The output signal of each individual detector is then applied to an amplifier from which it is applied, via an integration circuit and an analog-to-digital converter, to an electronic arithmetic device which reconstructs the absorption distribution of the irradiated body section from the measurement values thus obtained. It is then, inter alia necessary to combine the measurement values by convolution, after standardization and formation of the corresponding logarithm; this is also done in the electronic arithmetic device.

However, differences in the accuracy of adjacent amplifiers are likely to lead to artefacts (for example, ring patterns) in the reconstructed body section. In order to reduce the significance of such artefacts, complex electronic devices operating to a high accuracy are required for processing the detector output signals.

SUMMARY OF THE INVENTION

The invention has for its object to provide a device for determining the absorption distribution of radiation in a flat examination zone in a body in which less accurate electronic devices can be used for processing the detector output signals, without causing the appearance of artefacts in the reconstructed image.

This object is achieved in accordance with the invention in that at least a part of the detector array there are provided means which, for each pair of adjacent detectors, form a difference measurement value which is proportional to the difference between the non-amplified detector output signals, at least one detetor of this part being additionally connected to further means which form an absolute measurement value which is proportional to its detector output signal, adding means being provided for adding the difference measurement value to the absolute measurement value.

If an absolute measurement value M1 which is proportional to a detector output signal is known, for example, by direct measurement by means of a detector of the detector array which is situated at the extremity or in the centre, and if the difference between the non-amplified detector output signals of each pair of adjacent detectors is directly formed, for example, by connecting the outputs of each pair of adjacent detectors to a differential amplifier which operates as a subtraction member, so that difference measurement values (M2−M1), (M3−M2), ... are formed, continuous addition of the difference measurement values to the absolute measurement value can be used to determine further absolute measurement values $\overline{M2} = \overline{M1} + (M2-M1)$, $\overline{M3} = \overline{M1} + (M2-M1) + (M3-M2)$, etc. for the other detectors, the latter values corresponding to the values which would have been obtained by direct measurement of the absolute measurement value of each individual detector. The absolute measurement values $\overline{M2}$, $\overline{M3}$ ... formed by the addition contain the error incurred during the measurement of the first absolute measurement value $\overline{M1} = \overline{M1}$. However, this error is unimportant because it occurs in all the measurement values, so that it does not contribute to the formation of artefacts. However, any errors which occur due to the direct formation of the difference between the detector output signals and which are dependent on errors in the gain factor of the differential amplifiers and the difference between the detector output signals will be comparatively small and, moreover, they may average out during the addition of the difference measurement values.

Thus, by the direct formation of the difference between the detector output signals it is achieved that the accuracy of the amplifiers which amplify the detector output signals may be lower and still satisfy the same requirements as regards the artefact content of the reconstructed absorption distribution. The absolute measurement values $\overline{M1}$, $\overline{M2}$, $\overline{M3}$ ... can then each be applied to the electronic arithmetic device via an analog-to-digital converter or via an analog-to-digital converter which is common to all the measurement values.

In a preferred elaboration in accordance with the invention, the adding means are connected to the outputs of the analog-to-digital converters for the addition of the digitized difference measurement values (M2−M1), (M3−M2), ... ) to the digitized absolute measurement value M1. The difference measurement values (M2−M1), (M3−M2), ... and the absolute measurement value M1 are thus applied to an analog-to-digital converter prior to addition. It is thus achieved that the analog-to-digital converters may have a smaller resolution, i.e. a smaller bit number, in comparison with those of the known arrangement.

THE DRAWINGS

The drawing shows embodiments in accordance with the invention. Therein:

DESCRIPTION OF A PREFERRED EMBODIMENT

Figure 1:
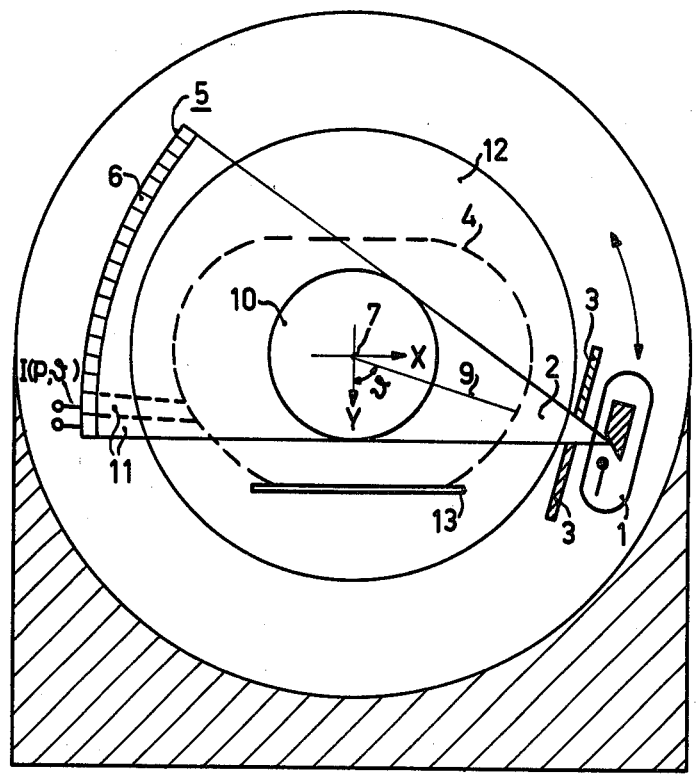
FIG. 1 shows a known computer tomography apparatus.

FIG. 1 is a diagrammatic sectional view of an X-ray tomography apparatus which comprises a radiation source 1 for emitting a fan-shaped X-ray beam 2 which extends in the sectional plane representing the examination plane, and which is limited by means of a diaphragm 3. The X-ray beam 2 penetrates a body 4 under examination and is incident on a detector array 5 which consists of individual radiation detectors 6 which are adjacently arranged in the plane of examination. The system formed by the radiation source 1 and the detector array 5 is rotatably arranged about a central axis 7 which extends perpendicularly to the examination plane, its position with respect to a rectangular system of coordinates X, Y which is situated in the plane of examination being denoted by angle of rotation $\theta$ which is enclosed by the central ray 9 of the fan-shaped radiation beam 2 and the Y-axis, while P indicates the distance between a beam path and the coordinate origin. The origin of the coordinate system X, Y through which the central axis 7 extends, at the same time forms the centre of the examination zone 10 of the X-ray tomography apparatus. This is the zone in the examination plane which is fully irradiated at any angle of rotation $\theta$, the width of the beam paths 11 being determined by the width of the detectors 6. The detector output signals are denoted as I $(p,\theta)$ and correspond to the absorption of the radiation along the beam paths 11.

A patient table 13 which is displaceable perpendicularly with respect to the examination plane, is provided for positioning the body (denoted by broken lines) to be examined in a positioning zone 12 which is concentric with the examination zone 10. The mechanical journalling is not shown for the sake of simplicity. Moreover, by changing the position of the body 4 within the positioning zone 12, it can be achieved that the examination zone 10, whose size can be changed by adjustment of the diaphragm 3, will cover various regions within the body 4 to be examined. To achieve this, of course sufficient clearance must be present between the body 4 and the positioning zone 12.

Figure 2:
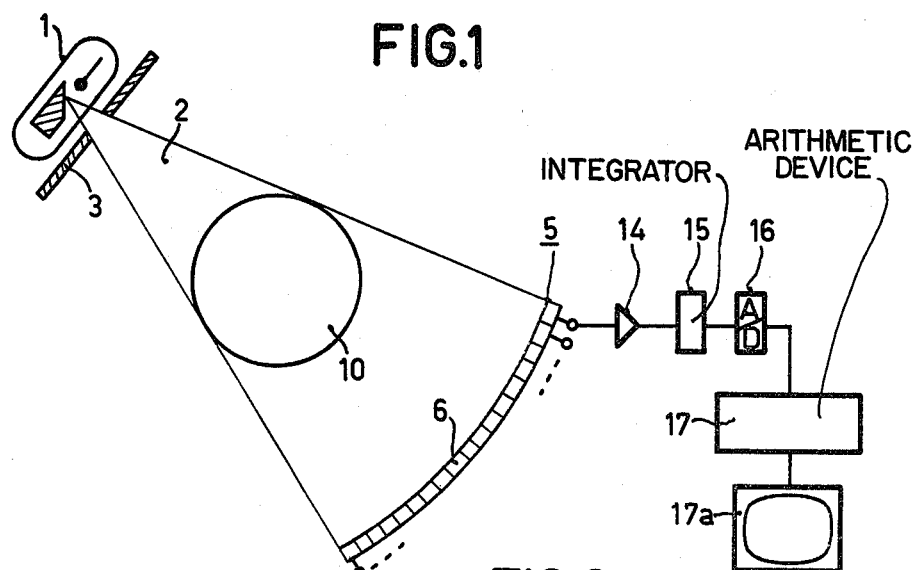
FIG. 2 shows a detector array with known signal processing.

FIG. 2 shows how the detector output signals I(p,$\theta$) are electronically processed in known manner. Each of the outputs of the individual detector 6 is respectively connected to an amplifier 14 via which the detector output signals are applied to an integrator 15 and to an analog-to-digital converter 16, so that at the output of the analog-to-digital converter absolute, digitized measurement values are present. The measurement values are subsequently applied to an electronic arithmetic device 17 for the reconstruction of the absorption distribution, said arithmetic device being connected, for example, to a monitor 17a for displaying the absorptin distribution. Thus, such a succession of electronic units (14-16) is connected to the output of each detector 6, it being possible for the amplifier 14 and the integrator 15 to be combined so as to form one unit.

Figure 3:
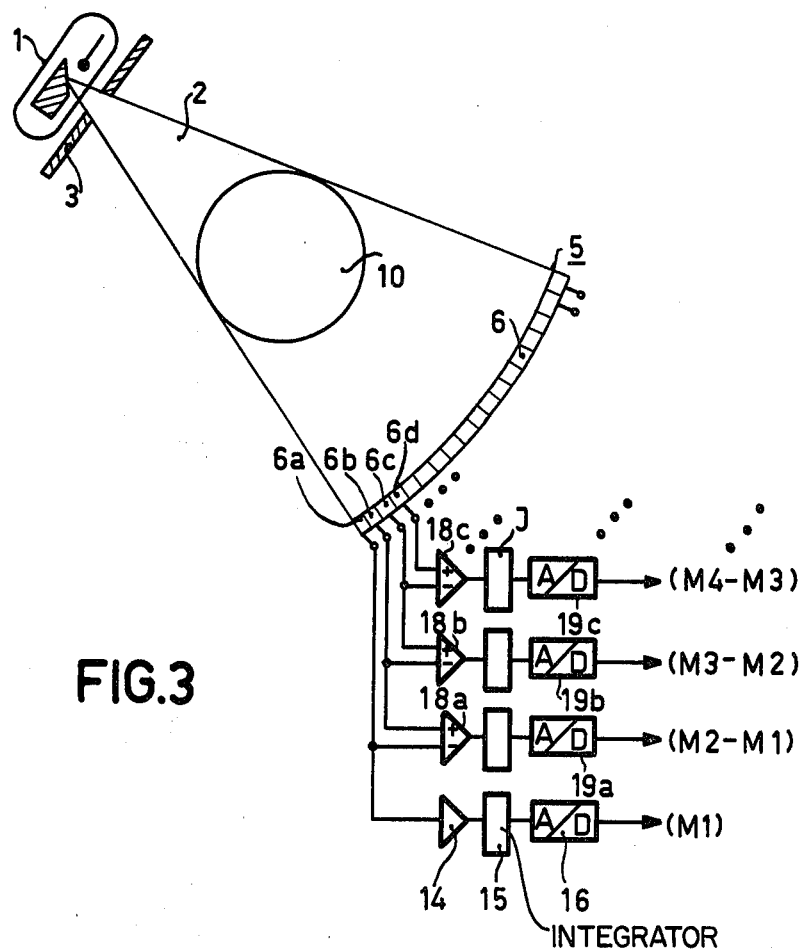
FIG. 3 shows a detector array with means for forming the difference between the detector output signals.

If less accurate amplifiers and analog-to-digital converters are to be used for the processing of the detector output signals without giving rise to artefacts in the image to be reconstructed, a device as shown in FIG. 3 is used in accordance with the invention, in which the difference between the non-amplified detector output signals I(p,$\theta$) of each pair of adjacent detectors 6a, b; 6b, c etc. is formed directly. To achieve this, for example, differential amplifiers 18a, b, c, . . . , are used. In general this does not imply an additional expenditure, because present day amplifiers often include a difference input which, if not employed, would be connected to zero potential. For the application of the invention it is not important whether the amplifiers 18a-c etc. are solely linear amplifiers or also include integrators. It is only important that the formation of the difference between the detector output signals I(p,$\theta$) takes place at the input of the amplifiers.

The output signals of the differential amplifiers 18a-c . . . are applied to analog-to-digital converters 19a-c, . . . via integrators I. Digitized difference measurement values (M2−M1), (M3−M2) etc. then appear at the outputs of said converters. In addition, however, on one or more detectors of the detector array 5, for example the outer detector 6a, an absolute measurement value M1 which is proportional to the detector output signal, is measured. For this purpose detector 6a is additionally connected to an amplifier 14, an integrator 15 and an analog-to-digital converter 16, at the output of which a digitized absolute measurement value M1 appears which corresponds to the detector output signal.

The determination of absolute measurement values $\overline{M2}$, $\overline{M3}$ . . . for the other detectors 6a, c, d, etc, which are standardized and whose logarithm is formed in the arithmetic device 17 prior to convolution, is performed so that the relevant digitized difference measurement values (M2−M1), (M3−M2), . . . are added to the absolute digitized measurement value M1(M1=$\overline{M1}$). For example, $\overline{M2}$ is obtained for the detector 6b in accordance with the formule $\overline{M2}$=M1+(M2−M1) when the detector 6b is the second detector in the detector array 5, and (M2−M1) is the difference measurement value derived from the detector output signals of the second and the first detectors 6b, a.

For the third detector 6c of the detector array 5, the absolute measurement value $\overline{M3}$ is obtained as $$\overline{M3} = M1 + (M2 - M1) + (M3 - M2),$$

where (M3−M2) is the difference measurement value derived from the detector output signals of the third and the second detector 6c, 6b. For the further absolute measurement values $\overline{M4}$ . . . , etc. the same is applicable.

The error contained in the measurement value M1, of course, will also appear in all further absolute measurement values calculated. However, it will not contribute to the formation of the artefacts, because it is present in all measurement values. The errors produced during the formation of the difference between the detector output signals, however, are very small and are generally averaged out during the calculation of the absolute measurement values from the difference measurement values. Therefore, less accurate amplifiers 14, 18a, 18b, c (and integrators 15, I) can be used.

Because furthermore the difference measurement values (M2−M1), (M3−M2), . . . or the absolute measurement value M1 are added together only after having passed through the analog-to-digital converters 16, 19a-c . . . , the analog-to-digital converters may also have a lower resolution, i.e. a smaller bit number, than those of the known arrangement.

Figure 4:
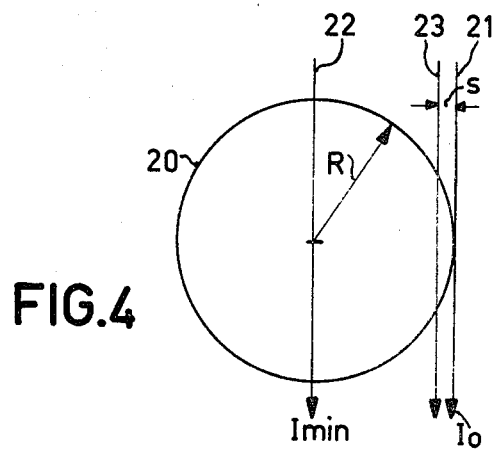
FIG. 4 illustrates the resolution in analog-to-digital converters.

This will be explained with reference to FIG. 4 which shows an object 20 having a radius R = 15 cm and an absorption $\mu$ = 0.2 cm$^{-1}$ (i.e. water). The intensity outside the object is assumed to be $I_o$, measured by the beam 21. The minimum intensity is $I_{min}$, measured by the beam 22. For the given values:

$$I_{min} = I_o e^{-2\mu R} = I_o e^{-6} = 0.00248 I_o.$$

If this value is to be measured with an accuracy of approximately 1°/$_\infty$ the measurement signal of the known arrangement may have a relative error (for example, due to amplifier drift) of only approximately 2.48×10$^{-6}$. This necessitates very accurate amplifiers and an analog-to-digital converter having a resolution of approximately 20 bits.

When the difference between the non-amplified detector signals is formed, the relative errors with respect to the difference measurement values (M2−M1), (M3−M2), ... may be larger, so that analog-to-digital converters having a lower bit number can be used.

The largest difference $I_{max}$ of the measurement values occurs at the contour of the object when a ray just misses the object (the ray 21) and the adjacent ray 23, situated one detector width s further in, strikes the object 20. The path length through the object 20 is $$\sigma = 2\sqrt{R^2 - (R-s)^2} = 2\sqrt{s(2R-s)}.$$

When the ratio 2R/s is indicated as N which gives the number of detector elements covering the object:

$$\sigma = 4R\sqrt{\frac{N-1}{N}}.$$

For N=200, the intensity difference is then $$\Delta I_{max} = I_o - I_o e^{-\mu\sigma} = I_o(1 - e^{-\mu\sigma}) \approx 0.5 I_o$$

However, in practice an essentially smaller value of approximately $\Delta I_{max} \approx 0.2 I_o$ occurs, for example, due to the widened radiation geometry.

This results in a larger relative error (proportional to $1/\Delta I_{max}$), so that several bits can be saved for an analog-to-digital converter.

The proposed method produces an essential advantage in the vicinity of the centre of rotation, because in that region $\Delta I_{max}$ is always much smaller, so that further bits can be saved for an analog-to-digital converter or amplifiers of lower quality suffice.

In order to ensure that the calculated absolute measurement values M1, M2, M3, ... do not depart too much from the actual measurement values, the absolute measurement values of a plurality of detectors which are distributed over the detector array 5, can be additionally measured. If differences appear between individually measured measurement values and the absolute measurement values calculated by means of the difference measurement values, this error is distributed as uniformly as possible over many measurement values, so that its effect is reduced. Individual absolute measurement values can be measured by further arrangements as shown in FIG. 2 (elements 14–16) which are additionally connected to the detectors 6.

Figure 5:
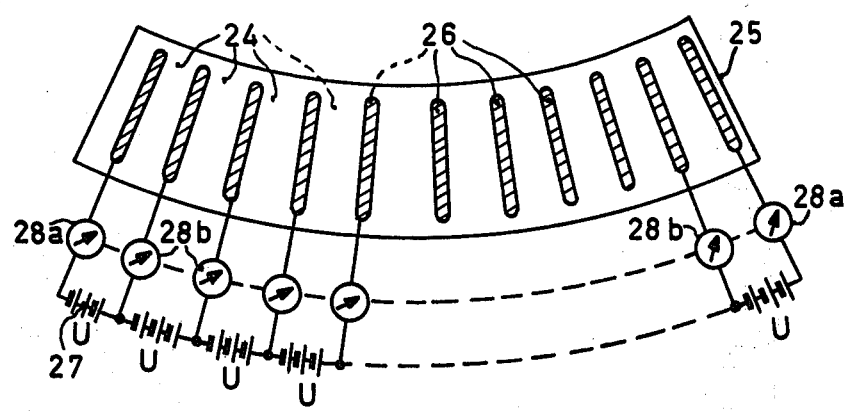
FIG. 5 shows a detector array consisting of ionization chambers for the direct formation of the difference between the detector output signals.

According to an elaboration in accordance with the invention, it is possible to construct detector elements which directly form the difference between the detector output signals directly in order to avoid the process of difference formation which must also be very accurate. FIG. 5 shows such an embodiment. A chain of ionization chambers 24, forming a detector array 25, receives voltages U. The voltage U increases in a cascade-like manner in equal amounts from one electrode plate 26 to the next in one direction across the detector array 25. The electrode plates 26 are arranged at the same distance from each other. The necessary power supply is only diagrammatically denoted by batteries 27, and the measurement apparatus 28a, b measure the ionization current. The measurement apparatus 28a then indicates the absolute measurement values, while the measurement apparatus 28b indicates each of the difference measurement values. The amplifiers are then at potentials which amount to a multiple of U, i.e. the measurement values must be extracted, for example, by optical couplers. An excessively large potential difference, however, can be prevented, for example, by the alternating activation of the voltage sources.

Figure 6:
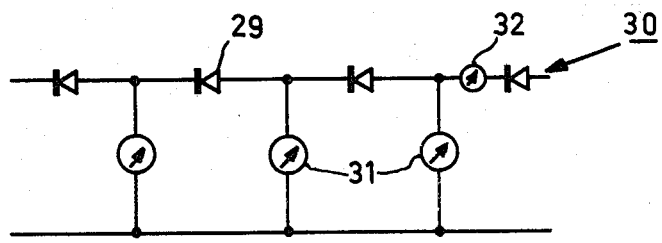
FIG. 6 shows a further detector array which consists of photodiodes.

Similar arrangements are also possible in detector arrays which comprise, for example scintillators with optically coupled photodiodes 29, cascading being facilitated because of the essentially lower voltages. FIG. 6 shows such a diode array 30, in which the diodes 29 are operated in the short-circuit mode. Each time between two diodes 29 and a potential which is common to all diodes 29 there is arranged a measurement apparatus 31 for measuring the currents which flows in opposite directions for each adjacent pair of diodes 29, the measurement apparatus 31 indicating difference measurement values. By means of the measurement apparatus 32, however, which measures only the current through one diode, an absolute measurement value is formed.

What is claimed is:

1. In a device for determining the absorption distribution of radiation in a flat examination zone in a body, comprising:
   a radiation source which is rotatable about the body and which emits a fan-shaped radiation beam which extends in the plane and which completely irradiates the examination zone from different directions;
   a detector array which comprises individual detectors for generating detector output signals which are a measure of the absorption of radiation;
   means for amplifying the detector output signals;
   analog-to-digital converters for converting the amplified signals to digital form; and
   means for generating and displaying the absorption distribution from the detector output signals; the improvement comprising:
   means connected to at least a part of the detector array which, for each pair of adjacent detectors therein, form a difference measurement value which is proportional to the difference between the corresponding, non-amplified detector output signals;
   further means, connected to at least one detector of said part, which form an absolute measurement value which is proportional to its signal; and
   adding means which add the difference measurement value to the absolute measurement value.

2. A device as claimed in claim 1, wherein the adding means are connected to the outputs of the analog-to-digital converters in order to add the digitized difference measurement values to the digitized absolute measurement value.

3. A device as claimed in claim 1 or 2, further comprising subtracting means, connected to the outputs of each pair of detectors which form the difference measurement values from the detector output signals.

4. A device as claimed in claim 3, wherein the subtracting means comprise a differential amplifier.

5. A device as claimed in claim 3 wherein the subtracting means are provided only for detectors which are situated in the central part of the detector array.

6. A device as claimed in claim 1 or 2, wherein the detector array consists of a row of ionization chambers which function as individual detectors and is formed by a series of electrode plates which are uniformly spaced and further comprising means for providing a voltage on the electrode plates which increases in a cascade-like manner by equal amounts along the detector array, and measurement means connected between the means for providing a voltage and the corresponding electrode plates for measuring the ionization current flowing to or from the relevant electrode plate to form the difference measurement values from the detector output signals.

7. A device as claimed in claim 1 or 2, wherein the individual detectors comprise photodiodes which respond to X-rays and which are connected one after another to form a detector array; measurement means which measures the short-circuit current of each adjacent pair of diodes connected between a common connection to the pair of diodes and a potential which is common to all diodes to form the difference measurement values, and one further measurement means connected between at least one further diode pair for measuring the current flowing through one of the diodes.

8. A device as claimed in claim 4 wherein the subtracting means are provided only for detectors which are situated in the central part of the detector array.

* * * * *